US011052390B1

(12) United States Patent
Bernhards et al.

(10) Patent No.: US 11,052,390 B1
(45) Date of Patent: Jul. 6, 2021

(54) AERODYNAMIC BIOLOGICAL ASSAY DEVICE FOR EXPLORATORY DETECTION

(71) Applicant: Combat Capabilities Development Command, Chemical Biological Center, APG, MD (US)

(72) Inventors: Robert C Bernhards, Abingdon, MD (US); Phillip M. Mach, Edgewood, MD (US); Kathleen J Quinn, Clifton, VA (US); Trevor G Glaros, North East, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 282 days.

(21) Appl. No.: 16/444,511

(22) Filed: Jun. 18, 2019

Related U.S. Application Data

(60) Provisional application No. 62/686,916, filed on Jun. 19, 2018.

(51) Int. Cl.
*B01L 3/00* (2006.01)
*C12Q 1/6844* (2018.01)
*G01N 33/58* (2006.01)

(52) U.S. Cl.
CPC ........ *B01L 3/50273* (2013.01); *C12Q 1/6844* (2013.01); *G01N 33/582* (2013.01); *B01L 2200/10* (2013.01); *B01L 2300/023* (2013.01); *B01L 2300/08* (2013.01); *B01L 2300/087* (2013.01); *B01L 2300/0851* (2013.01); *B01L 2300/12* (2013.01); *B01L 2300/123* (2013.01); *B01L 2300/126* (2013.01); *B01L 2400/0409* (2013.01); *B01L 2400/0627* (2013.01)

(58) Field of Classification Search
CPC ............ B01L 3/50273; B01L 2300/12; B01L 2300/08; B01L 2300/087; B01L 2300/123; B01L 2300/126; B01L 2300/023; B01L 2200/10; B01L 2400/0627; B01L 2300/0851; B01L 2400/0409; C12Q 1/6844; G01N 33/582
See application file for complete search history.

(56) References Cited

U.S. PATENT DOCUMENTS

| 7,811,520 B2 * | 10/2010 | Bernhardt | ............ G01N 1/2226 422/83 |
| 2005/0142662 A1 * | 6/2005 | Bonne | .................... G01N 30/12 436/149 |

\* cited by examiner

*Primary Examiner* — Jennifer Wecker
*Assistant Examiner* — Jonathan Bortoli
(74) *Attorney, Agent, or Firm* — Ulysses John Biffoni

(57) ABSTRACT

The invention is directed towards an Aerodynamic Automated Biological Assay Device ("AABAD") comprising an aerodynamic substrate having a microfluidic cassette and an electronic module, and a system and a method of deploying the same to detect biological agents and hazards suspended in an atmosphere. The AABAD may be in the form/shape of a maple seed/fruit to induce autorotation. A plurality of AABADs are dispersed into the atmosphere from an aircraft or drone. The AABADs rotate via centrifugal forces without motor or active propulsion system while descending to the ground, wherein during the descent, the AABADs microfluidic cassettes collect and process the air samples via a centrifugal force formed from the autorotation generated by the airborne carrier, and to analyze and transmits the results to a remote location.

22 Claims, 5 Drawing Sheets

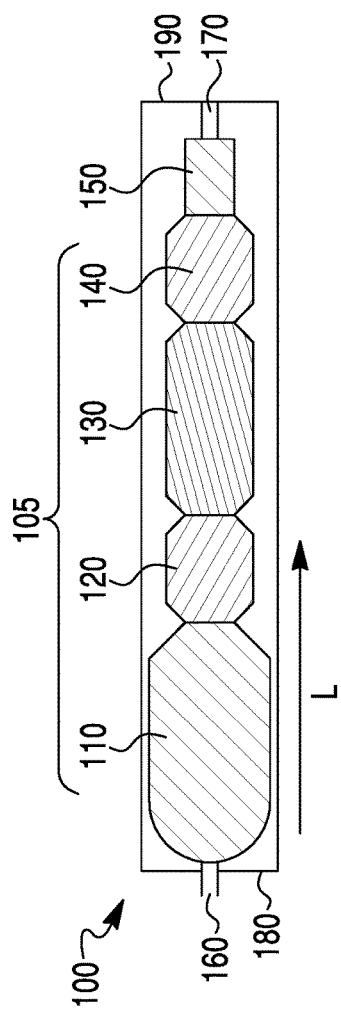
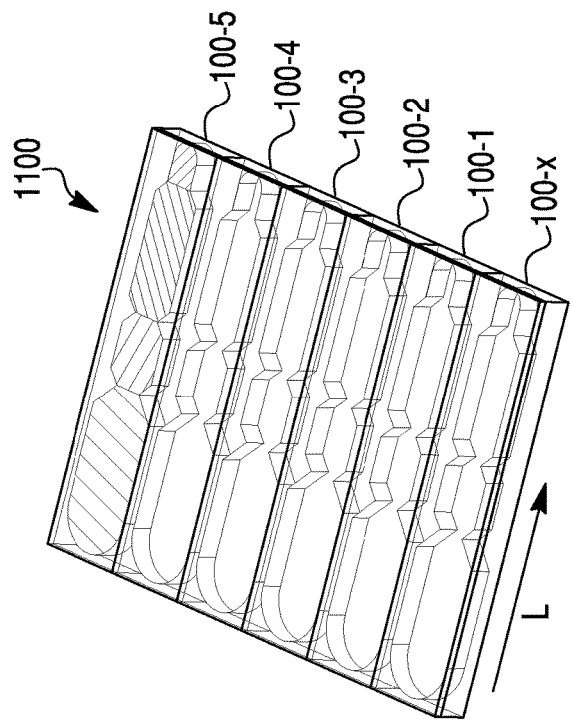
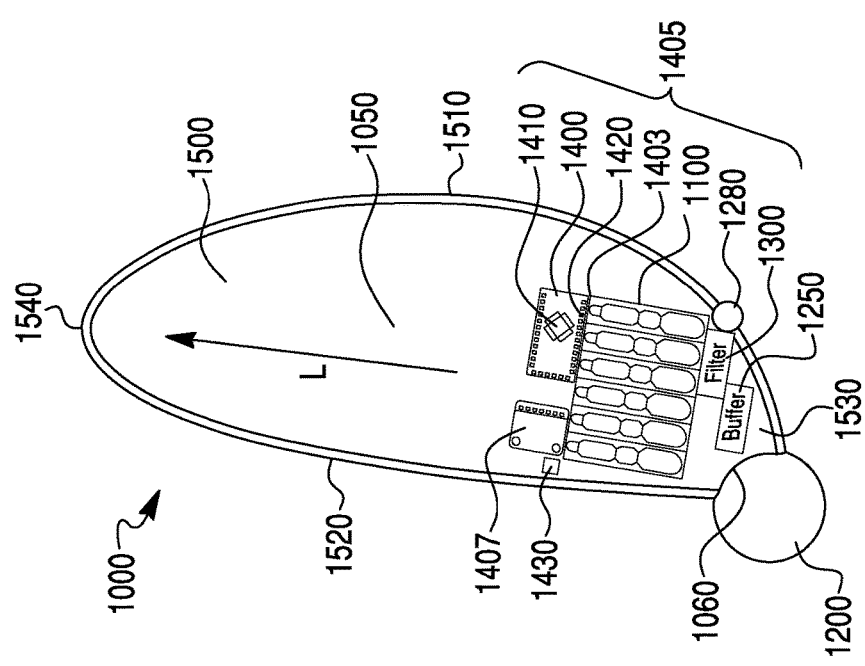

AERODYNAMIC BIOLOGICAL ASSAY DEVICE FOR EXPLORATORY DETECTION

PRIORITY CLAIM

This application makes reference to, incorporates by reference herein, and claims the benefit of U.S. Provisional Application No. 62/686,916 filed on Jun. 19, 2018.

GOVERNMENT INTEREST

The invention described herein may be manufactured, used and licensed by or for the United States Government.

FIELD OF THE INVENTION

This invention pertains to a safe, efficient, automated, real-time detection device, its system and method for detecting biological materials suspended in an atmosphere of an unknown threat environment.

BACKGROUND OF THE INVENTION

Biological Assays serve varying needs, from detection of diseases in what is known as ERISA (enzyme-linked immunosorbent assay) and Immunoassays to forensic DNA analysis to detection of biological hazardous agents. Some of these biological agents are present in the environment or body fluids, while other biological agents may be deployed and suspended in an airborne plume. Biological hazardous agents may include terrorism and/or wartime biological weapons, such as *Yersinia pestis* and *Bacillus anthracis*, et al., which would endanger combat troops or populations situated nearby.

Current technology includes portable devices that detect for such biological threats. Some of these devices do not require mixing the biological agent in a liquid, while other devices require testing sample to be arranged in liquid prior to the assay. In recent years, microfluidic technology has provided a compact and efficient means for biological assay.

Deployable and automated biological assay devices based upon isothermal amplification and microcontrollers have become highly accurate and cost effective. Molecular analysis is performed from a given sample in an automated fashion utilizing a single-use microfluidic cassette and a positive/negative detection strategy. Some units utilize rotational motion to transport the sample within microfluidic wells, wherein each well performs a given operation of the sample preparation or molecular analysis. Low-power thermal modules and novel fluorescence-sensing modules are integrated into these analyzers. This configuration enables real-time monitoring of loop-mediated isothermal nucleic acid amplification ("LAMP") of biological agents. Currently developed state-of-the-art prototypes, such as the AnyMDx system developed at Pennsylvania State University, utilize microcontrollers that perform a variety of functions to coordinate the processes needed to perform the sample preparation and LAMP procedure. The motion of the AnyMDx device coordinates the movement of DNA bound to pH charge switchable magnetic beads between each reaction chamber as steps in the sample preparatory procedure are accomplished. Precise timing of the rotation and activation of electromagnets in tandem enable movement of sample from chamber-to-chamber. During the LAMP assay, the detection of DNA amplicons bound by a fluorescent dye is achieved via LED excitation and using an optical sensor to detect the intensity of relative fluorescence units (RFUs) emitted from the sample in real time.

However, when the targeted biological agent is suspended in the atmosphere, the AnyMDx is not useful, as the AnyMDx does not collect the sample or perform cell lysis on the collected sample without motor. These tasks are left to a user, which makes the AnyMDx inappropriate for detecting biological hazards suspended in air of an unknown threat environment as it may pose a threat to the users who collect the samples. Furthermore, the AnyMDx requires magnetic beads to be mixed with the lysate and then removed from the lysate to facilitate movement of the lysate containing the collected sample through the microfluidic device.

There are other attempts known in the art, U.S. Pat. No. 7,530,257 to Bonne pertains to a fluidic microanalyzer that includes a battery and a heater, such that a fluidic microanalyzer is incorporated in an unmanned aerial vehicle (UAV). U.S. Pat. No. 7,073,748 to Maurer, et al. pertains to a UAV including a sensor on board to detect wartime biohazards. The UAV has an intake to collect the sample, excites the sample with UV radiation, and measures a fluorescence characteristic of the sample. The UAV may also include a radio transmitter and a GPS for relaying results and determining location respectively. U.S. Pat. No. 10,209,188 to Ng et al. pertains to a device in a drone or UAV to detect hazards such as bio-contaminants in an atmosphere and wirelessly communicate said results back to a remote location. A GPS, light source and detector are used to determine location and detect a targeted agent respectively. No microfluidic or lab on chip is used in Ng et al., U.S. Pat. No. 6,442,997 to Megerle et al. pertains to a RAM air collector arranged within an UAV to collect chemical and biological hazards for detection in a battle situation. The RAM air sample mechanism replaces the heavier fans and blowers. No dispersal of probes or inclusion of microfluidic or lab-on-chip technology is disclosed in Megerle et al.

However, in each of the above cited references, a drone or UAV must fly through an atmosphere containing the contaminant in order to obtain a sample of the contaminant for measurement. This is undesirable as the sample size is limited because only one device collects the sample, and if the drone misses the biohazard by failing to fly through the contaminated plume region, an incorrect result may be obtained, subjecting troops nearby to even a greater hazard. Furthermore, if the above were inserted into a drone to collect an air sample, the drone itself may be contaminated and will therefore need to be destroyed before it returns to base.

U.S. 2014/0043172 to Montobianco et al. describes a drifting airborne probe that includes a body having an aerodynamic shape of a wind dispersible natural seed. The probe includes a total mass of less than 10 grams, a power source operably connected to the body; at least one sensor operably connected to the body for collecting data from the environment and about the environment, and a transmitter for transmitting the data operably connected to the body and no active propulsion system.

Montobianco et al. does not teach or suggest an airborne automated sample analyzer that utilizes natural force to perform assays. U.S. Pat. No. 7,811,520 to Bernhardt describes a method for collecting and sensing a column of air in near real-time to detect one or more agents dispersed within the air column. The method includes passing the column of air through a port in a parafoil, the parafoil configured with a flow-through sensor suite located in the port and operable such that the column of air passes through the sensor suite, operating the sensor suite to test the column of air for the one or more agents, and receiving test results from the sensor suite. No microfluids devices are used in Bernhardt, and the parafoil itself does not do the sensing but requires separate nanosensors to be dispersed.

U.S. 2006/0188399 to Smid pertains to a piezoelectric analytic sensor system, that when exposed to an analyte, determines the analyte mass, and can be dispersed by a low flying aerial vehicle to detect hazards such as chemical warfare agents and relay the results via wireless communication. Smid is silent on automation of assay while airborne induced by natural forces.

U.S. Pat. No. 4,886,222 to Burke (NASA) pertains to an atmospheric autorotating imaging device that includes a central housing and a single wing that rotates about the housing for stable flight. On board is a camera, and possibly solar panels, a battery, and radio transmitting capabilities. U.S. Pat. No. 8,205,822 to Jameson et al. pertains to an UAV that resembles a maple seed mono-copter with a wing or airfoil that rotates about a center but includes a propulsion device and thus does not autorotate to deliver a payload.

None of the above cited references include a mechanism to detect and analyze biohazard materials utilizing natural forces, i.e. gravity, aerodynamic airflow and autorotation for sample assaying. Specifically, none of the references disclose or teach a microfluidic technique of, or relating to, release and dispersal of a large number of microfluidic devices into an atmosphere to determine from a distance whether a plume contains at least one biological threat.

Therefore, there is a need for reducing payload and cost by using natural forces to perform biological assay of biological threats in real time. Further there is a need to disperse a plurality of non-motorized bioassay devices into the atmosphere to test for biological threats suspended in the air without a motor, and to transmit the results from the assay to a remote and safe location.

SUMMARY OF THE INVENTION

The present invention is directed towards an Aerodynamic Automated Biological Assay Device ("AABAD") that includes 1) a substrate having a top and a bottom surfaces, a first distal end and a second opposing end, the second opposing end located near a center of mass of the AABAD, a center of lift located near a geometric center of the substrate; 2) a microfluidic cassette located on the top surface of the substrate between the second opposing end and the center of lift to analyze contents of an air sample from the earth's atmosphere; and 3) an electronic module located on the substrate at a location corresponding to the second opposing end, the electronic module includes a power source, a transmitter and an electronics package; and wherein a centrifugal force is produced along a length of the microfluidic cassette without motor or active propulsion system while the first distal end autorotates about the second opposing end due to airflow produced by the AABAD descending through the atmosphere to the ground.

The present invention is also directed towards a method for detecting a presence of at least one biological agent suspended in the earth's atmosphere, comprising 1) releasing a plurality of Aerodynamic Automated Biological Assay Devices (AABADs) into the earth's atmosphere from an aircraft; 2) the AABADs adsorbing or collecting the air samples while automatically rotating due to the centrifugal force generated by the airflow; 3) the AABAD analyzing the air samples while AABADs are airborne and rotating; and 4) the AABAD communicating wirelessly to a remote site results of the analysis of the air samples.

The present invention is also directed to a system for detecting biological materials suspended in the earth's atmosphere, the system including 1) an unmanned aerial vehicle ("AEV") that flies above an area that is contaminated by at least one biological agent; 2) a plurality of self-spinning, aerial dispersible AABAD devices containing microfluidic cassette to detect said at least one biological threat, such that AABAD's are released and dispersed by the AEV at a height above the contaminated area; and 3) a radio frequency receiver external to a region contaminated by one or more of the targeted biological agents ("TBAs") to receive test results from each of the plurality of AABADs.

BRIEF DESCRIPTION OF THE DRAWINGS

The invention, together with other objects, features, aspects and advantages thereof will be more clearly understood from the following in conjunction with the accompanying drawings.

FIG. 1 illustrates a plan view of the AABAD.

FIG. 2A illustrates a plan view of an individual test strip of the microfluidic cassette.

FIG. 2B illustrates a close-up view of a microfluidic cassette containing at least one test strip as shown in FIG. 2A.

DETAILED DESCRIPTION OF THE INVENTION

Figure 3:
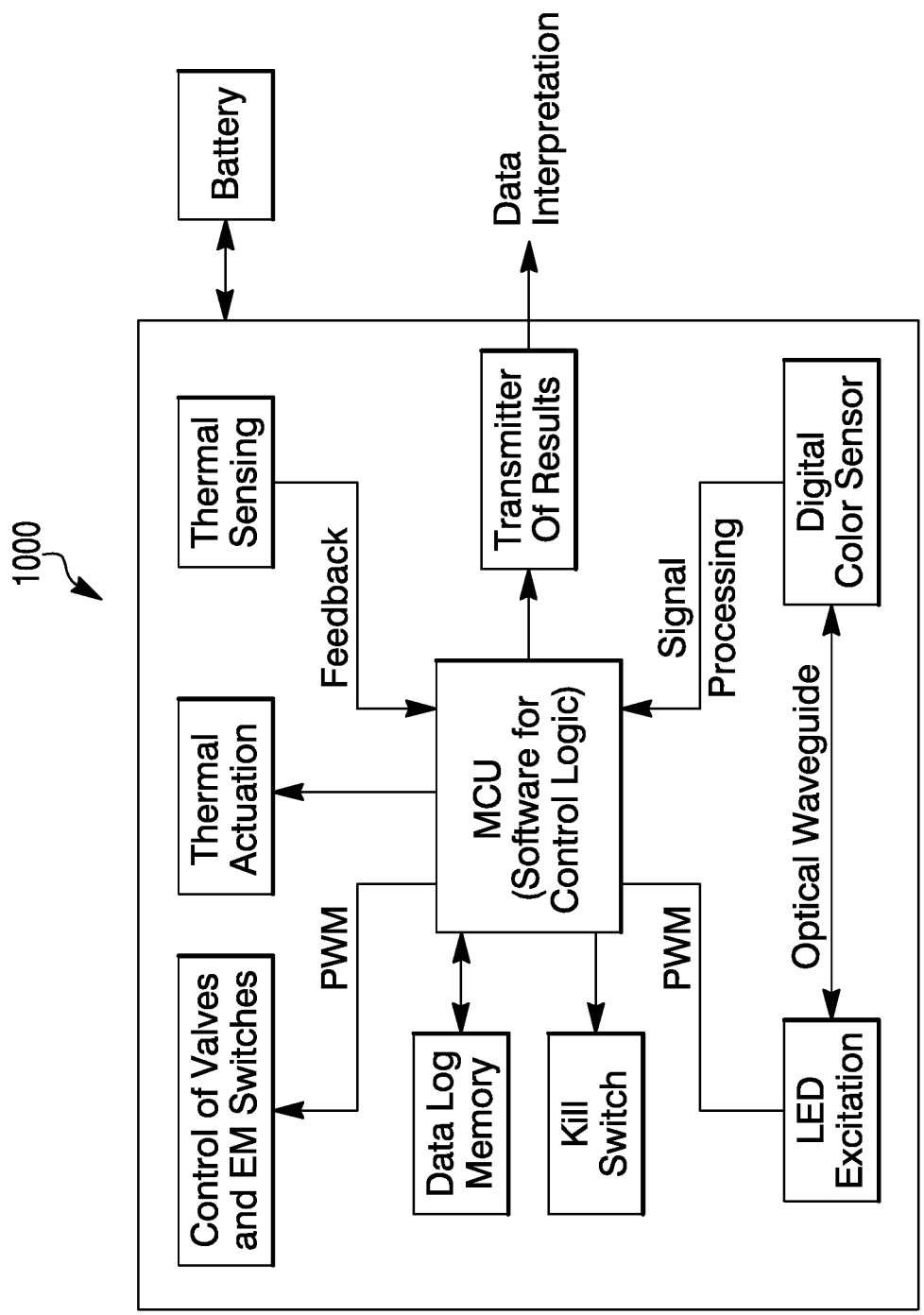
FIG. 3 is a block diagram of the AABAD modules and their interrelation to a microcontroller.

The novel aerodynamic automated biological assay device ("AABAD") 1000 is illustrated in FIG. 1 comprising a substrate 1500 attached to an electronics module 1200, with a plurality of sample processing apparatus 1405 mounted on substrate 1500. Substrate 1500 has a first distal end 1540 spaced apart from a second end 1530 opposing first distal end 1540 by a vector L of substrate 1500, vector L corresponding to a longitudinal length of substrate 1500 and a radial direction of AABAD 1000. A center of lift 1050 of AABAD 1000 is arranged between first and second ends 1540 and 1530 and is also arranged between a leading edge 1510 and an opposing, trailing edge 1520 connecting the first and second ends 1540 and 1530. A portion of substrate 1500 near leading edge 1510 has a greater mass than a portion of trailing edge 1520, such that first distal end 1540 of substrate 1500 spins about second opposing end 1530 in full 360 degrees in a direction such that said trailing edge 1520 trails said leading edge 1510.

The electronic module 1200 is arranged near second opposing end 1530 of substrate 1500 such that the electronic module 1200, in combination with a center of mass 1060, is heavier in mass by 1.15, 1.25, or at least 1.5 times the weight of a combination of substrate 1500 and sample processing apparatus 1405 mounted thereon, such that a center of mass (or center of gravity or center of rotation) 1060 is disposed near the electronics module 1200 and second opposing end 1530 of substrate 1500, while a center of lift 1050 is displaced a substantial distance in the L direction from the center of mass 1060.

Specifically, each AABAD 1000 autorotates at a rate of at least about 1800 rpm, preferably of at least about 2000 rpm, more preferably at least about 2500 rpm when dropped from an elevated height between 33,000 feet and 1,000 feet in order to produce a sufficient amount of centrifugal force to move the sample and the fluids through all portions of the microfluidic cassette 1100 mounted on substrate 1500 such that while the AABADs 1000 are airborne, AABADs 1000 collect and analyze the air sample. The modification of speed (rpm) and rotation is achieved by modifying the weight of the AABAD 1000, a location of the center of mass 1060, and/or by modifying a shape of the air foil of substrate 1500. Modification of the center of mass can be achieved by placing certain components on substrate 1500 as opposed to within electronics module 1200.

Electronic module 1200 includes, but not limited to power source, switches, valves, transmitter, electromagnetic gates and/or various other electronics to facilitate the analysis of the air samples. Electric module 1200 may also include a global positioning system ("GPS") and a buffering solution.

The power source is preferably a battery, and more preferably a coin-cell battery. Alternatively, a solar cell or commercial 1.5 Volt or 9 Volt batteries are also useful as the power source and still be within the scope of the present invention.

Also located near second end 1530 of substrate 1500 is a capture point 1280, a collection filter 1300, and a buffer tank 1250. The capture point 1280 preferably resides on leading edge 1510 of substrate 1500 and collects the air sample while the AABAD 1000 is spinning in mid-air. The collection filter 1300, adjacent to capture point 1280, receives the air sample from collection point 1280 by means of diffusion, passive transport, active transport or the like. Buffer tank 1250 includes a fluid to be described later that is released onto the filter 1300 to elute and prepare the collected air sample for amplification. The fluid in buffer tank 1250 flushes the microfluidic cassette 1100 and ensures filling of the channels 105 within microfluidic cassette 1100, to force movement of the collected air sample. The fluid within buffer tank 1250 may be water or some other buffer such as saline.

Microfluidic cassette 1100 is adjacent to collection filter 1300, and between center of mass 1060 and center of lift 1050. The microfluidic cassette 1100 of FIG. 1 has linear fluid pathways wherein the fluids and analyte move in a linear fashion via the centrifugal force generated by the AABAD 1000 spinning or rotating in mid-air. Specifically, a lengthwise direction of the fluid channels 105 of FIG. 2A in microfluidic cassette 1100 are arranged to extend in a direction that is parallel to longitudinal direction L, so that the channel direction within microfluidic cassette 1100 coincides with a direction of centrifugal force, when AABAD 1000 is spinning to allow the fluids and the analyte to progress through microfluidic cassette 1100 without needing any other mechanisms like magnetic beads to move the fluids and the analyte.

Also located on substrate 1500 of FIG. 1 and FIG. 2A is a plurality of sample processing apparatus 1405 comprising a printed circuit board ("PCB") 1400 arranged adjacent to a distal end of microfluidic cassette 1100, and a supplemental PCB 1407. Within PCB 1400 is a microcontroller 1410 and a detection module 1420. Connected to PCB 1400 is also a resistive heater (not illustrated) arranged underneath the LAMP reactors 150 of each test unit 100 of microfluidic cassette 1100 to heat to 65° C. Microcontroller 1410 may be a commercialized product known in the art. Microcontroller ("MCU") may control various functions within the AABAD as per the block diagram of FIG. 3. Detection module 1420 includes a light detector within. Detection module 1420 receives the DNA amplified biological sample containing the fluorescent dye from LAMP reactor 150 of microfluidic cassette 1100 via exit channel 170. A light source 1430, which preferably is an LED, illuminates the amplified sample within detection module 1420. The light detector within detection module 1420 senses whether or not the fluorescent dye introduced in LAMP reactor 150 illuminates upon being excited by light from LED 1430. The detector can be embodied as a color sensor, but in no way is the present invention limited thereto. It is to be appreciated that the detector faces the amplified sample in a direction orthogonal to a direction that light emerging from LED 1430 propagates in order to prevent the light emerging from LED 1430 from directly illuminating the detector within detection module 1420. Supplemental PCB 1407 acts as a fail-safe means, contains instruction for auto-destruction of AABAD, and/or contains transmitter for transmitting results. Alternatively, supplemental PCB 1407 may contain Interface electronics such as resistors, switches, wire bonds, etc. that required isolation from the effects of turbulence, liquid and frozen water as well as direct solar radiation.

FIG. 2A illustrates an individual test unit 100 arranged within the microfluidic cassette 1100 according to the first embodiment of the present invention. As illustrated in FIG. 2A, test unit 100 includes a first chamber 110, a first valving chamber 120, a second chamber 130, a second valving chamber 140 and a lamp chamber 150 sequentially arranged in the L direction of substrate 1500. The chambers together form channel 105. Microfluidic cassette 1100 includes one or more test units 100 arranged in parallel, as generally shown in FIG. 2B, a microfluidic cassette 1100 has a plurality of test units 100-1, 100-2, 100-3, 100-4, 100-5, 100-6 and 100-x, adjacent to one another. Alternatively, the test units may be spaced apart (not shown). The structure of each test unit 100-1 to 100-X is the same to ensure identical testing parameters.

The first chamber 110 of each test unit 100 prior to deployment of the AABADs 1000 contains a lyophilized Arcis™ reagent 1 (Arcis™ Biotechnology, Daresbury, United Kingdom), a second chamber 130 of each test unit 100 contains lyophilized Arcis™ reagent 2, and a LAMP reactor 150 contains amplification chemicals and a fluorescent dye to enable detection of the targeted biological agent in a subsequent detection chamber. The second chamber 130 is optional and all cell lysis can occur in a single chamber prior to passing the sample to chamber 150 for amplification, in which case only one valving chamber is required. Valving chambers 120 and 140 are in the form of an electromagnetic switch, a metering trap or the like, although a metering trap is preferred as such a technique is less prone to fail over time as compared to electrical or mechanical gating techniques. Test unit 100 is designed and oriented such that centrifugal force due to spinning of the AABAD 1000 enables the fluids and the analyte (i.e. collected air sample) to move into first chamber 110 via inlet 160, then second chamber 130, LAMP reactor 150, and subsequently into a detection area 1420 external to test unit 100 via outlet 170 at distal end 190, as illustrate in FIGS. 1 and 2A. The microcontroller 1410 on PCB 1400 controls the timing of operation of the gates or valves 120, and the release of the buffer solution from tank 1250, thereby controlling the amount of time the analyte and various fluids are incubated within any given chamber or reactor. Alternately, when the valves 120 and 140 are embodied as a metering trap, it is no longer necessary for the microcontroller 1410 to open up valves as they are done automatically by the width and height variations of the channel in a vicinity of a metering trap.

As illustrated in FIG. 2B, microfluidic cassette 1100 includes a plurality of test units 100-1, 100-2, 100-3, 100-4, 100-5, and **100-*x* arranged in parallel to each other and to the longitudinal L direction (parts 150 and 170 not shown). Although FIG. 2B illustrates 6 test units, it is to be understood that the present invention may include more or less, minimally one test unit 100 and a control test unit 100-X in microfluidic cassette 1100. Referring back to the microfluidic cassette 1100 illustrated in FIG. 2B, test unit 100-X is a negative control where no collected air sample passes through. Each of test units 100-1 to 100-5 are designed to all simultaneously receive the air sample in fluids, and to simultaneously detect an individual biological threat based on the reagents that are introduced into the corresponding LAMP reactors 150. In other words, more than one test unit may test for the same biological agent to create duplicates or triplicates, or, test unit 100-1 may test for one biological threat, test unit 100-2 may test for another biological threat and so on. Overall, test units 100-1 to 100-5** may test for the same or different biological agents such as *Yersinia pestis* (Plague), *Bacillus anthracis* (Anthrax), *Francisella tularensis* (Tularemia), *Clostridium botulinum* (Botulism), *Listeria monocytogenes* (Listeriosis), *Burkholderia mallei* (Glanders), *Shigella dysenteriae* (Dysentery), *Corynebacterium diphtheriae* (Diptheria), *Vibrio cholerae, Brucella suis* (Brucellosis bovine), *Brucella melitensis* (Brucellosis caprine) and *Brucella abortus* (Brucellosis porcine). With such a parallel design, each AABAD 1000 tests for many different biological threats simultaneously, thereby producing quick results in an efficient manner.

Figure 4:
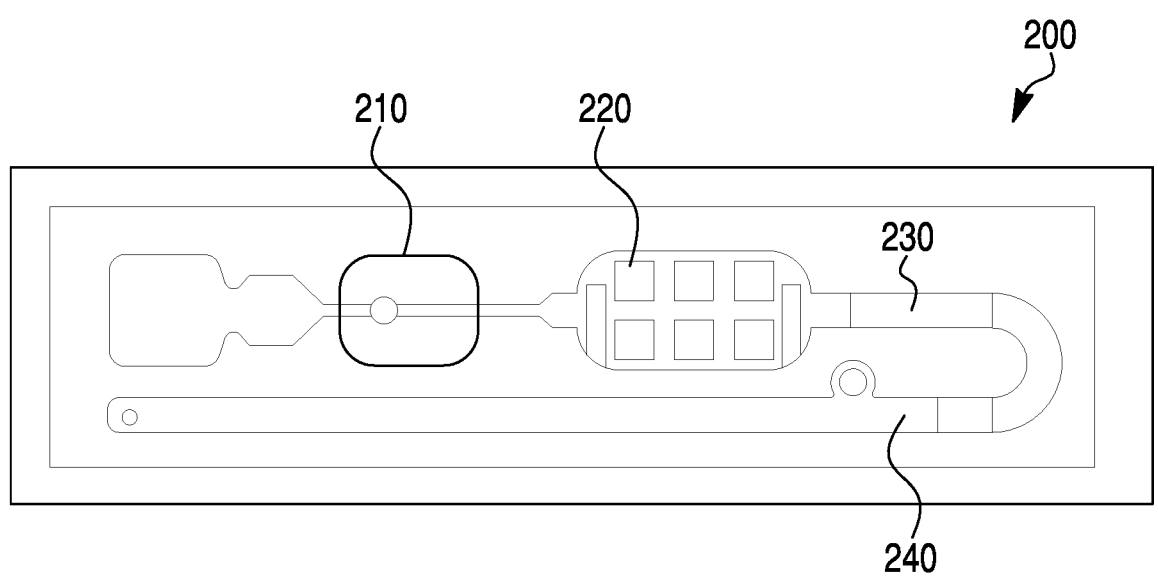
FIG. 4 illustrates a plan view of an alternative embodiment of an individual test strip of the microfluidic cassette.

In an alternative embodiment, at least one microfluidic cassette 1100 includes test units 200 as illustrated in FIG. 4. Instead of an electromagnetic gate for the valving chamber 120, as shown in FIG. 2A valve chamber 220 is in the form of a metering trap. A metering trap 220 is formed by widening a channel width just before the trap, and by blocking more than half of the cross-sectional area at the trap. Such metering trap controls the size and timing of testing droplet that can pass through. Overall, the metering mechanism increases dwell within a given region by using a 'maze' or transverse time. A pressure created from the centrifugal force is applied onto metering trap 220. As mentioned previously, the centrifugal force is created by the AABAD 1000 spinning at a speed of about at least 1800 rpm, preferably about at least 2000 rpm, more preferably about at least 2500 rpm.

Figure 5:
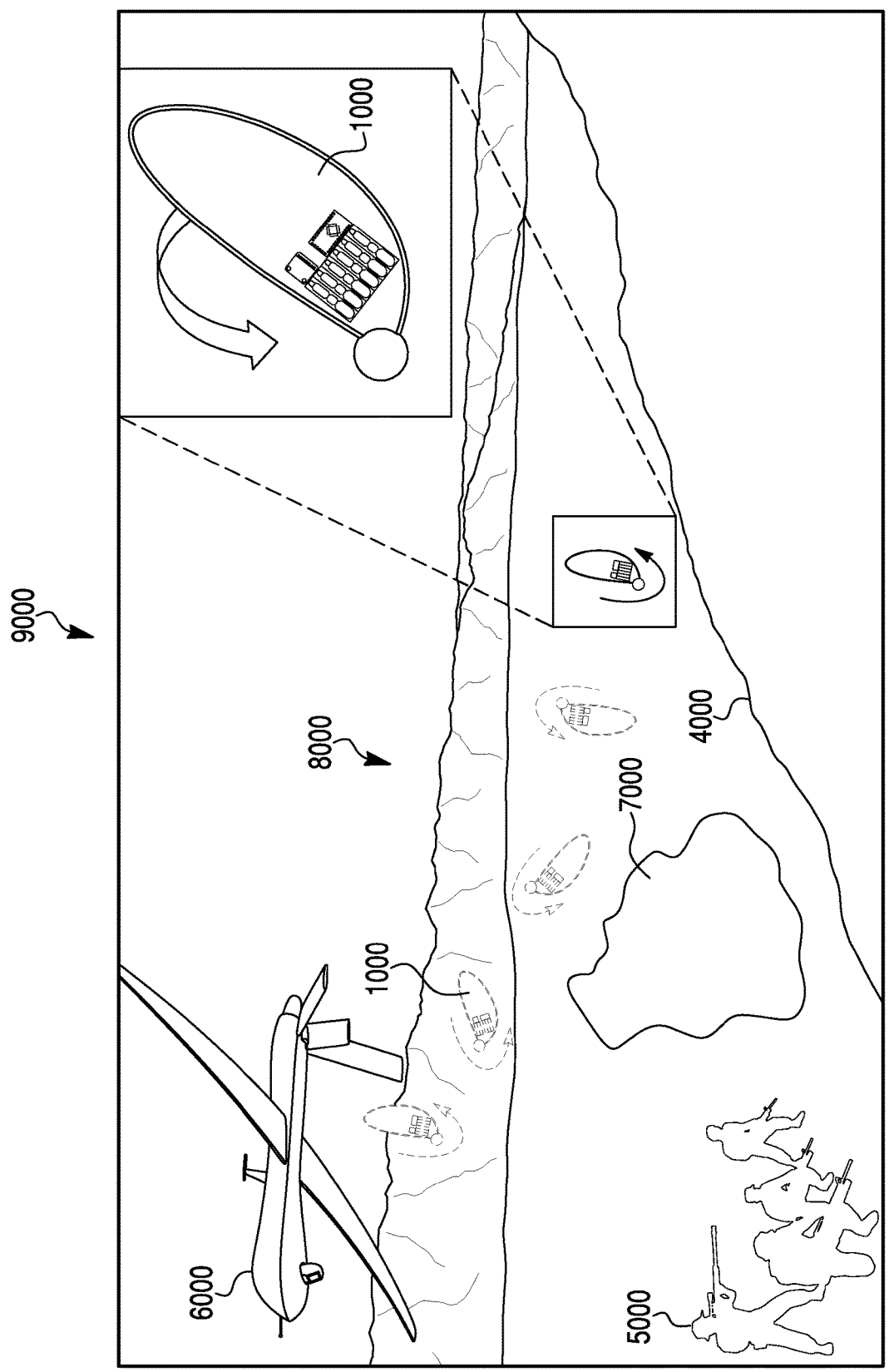
FIG. 5 illustrates a method and a system of detection of biological threats using at least one AABAD.

FIG. 5 illustrates the overall deployment system arrangement 9000 according to the principles of the present invention. As illustrated in FIG. 5, an aircraft 6000 is flown in an earth's atmosphere 8000 in a vicinity of a plume 7000 that is thought to be contaminated by biological agents near ground troops 5000. The aircraft 6000 is preferably an unmanned aerial vehicle (UAV) (i.e. a drone), but can also be a helicopter, an airplane, a glider, a balloon or the like and still be within the scope of the present invention. When near the plume 7000, aircraft 6000 releases a plurality of AABADs 1000 into atmosphere 8000 at an elevated height of between 33,000 feet and 1,000 feet, so that the AABADs 1000 disperse into atmosphere 8000 in a vicinity of plume 7000. The height at which aircraft 6000 releases AABADs 1000 depends upon weather conditions, the height of release preferably being beneath any atmospheric inversion layers in the atmosphere 8000. Upon being released, each of the AABADs 1000 are designed to automatically spin or rotate in a manner analogous to that of a Maple or Acer fruit upon slowly descending to the ground 4000, thereby imparting a centrifugal force along a longitudinal direction of each of the AABADs 1000.

Substrate 1500 preferably takes on a shape of an airfoil, but substrate 1500 may preferably also have the shape in the form of a maple tree (Acer) seed or fruit (samara), or a bird's wing, or a combination or a modification of these and still be within the scope of the present invention. Substrate 1500 may be a single layer upon which components are arranged or may be two layers where the microfluidic cassette 100 is arranged therebetween. A material for substrate 1500 may be selected from paper, plastic, Styrofoam, ceramic, metal and mixtures thereof. The longitudinal length L is less than 12 inches, preferably less than 8 inches, and more preferably less than 6 inches. The width of substrate 1500 is less than 8 inches, preferably less than 6 inches, and more preferably less than 4 inches. The weight of AABAD 1000 is between about 5 g to 5 kg, and preferably between 100 g to 3 kg, and even more preferably between 200 g to 1 kg. The dimension, material and shape of substrate 1500 allows for AABAD 1000 rotates about center of mass 1060, substrate 1500 produces a substantial amount of lift for the AABAD 1000, and can also spin at a rate of about at least 1800 rpm, preferably about at least 2000 rpm, more preferably about t least 2500 rpm, upon descending through the atmosphere 8000 at an elevation of between 33,000 feet and 1,000 feet. While spinning or rotating, AABAD 1000 descends through atmosphere 8000 and plume 7000 to allow for collection and analysis of the air sample prior to the AABAD 1000 hitting the ground 4000, thereby providing the centrifugal force to induce movements of fluids and the analyte within the microcassette 1100.

Method of Use

When a plume 7000 containing suspicious suspended material is first realized, an aircraft 6000, such as a UAV and carrying a plurality of AABADs 1000, is deployed to a vicinity of the plume 7000. Upon reaching a vicinity of the plume, the aircraft 6000 releases the plurality of AABADs 1000 into atmosphere 8000. These AABADs disperse through the atmosphere 8000, and many enter plume 7000. Upon descending to ground 4000, they autorotate about a center of mass 1060 at a high rate of about at least 1800 rpm, preferably at least about 2000 rpm, and more preferably at least about 2500 rpm.

Upon the AABADs 1000 descending and rotating through atmosphere 8000, filter unit 1300 located on substrate 1500 is initialized to collect air samples from plume 7000. After about 2 minutes of collection, a valve is opened to allow an eluent, such as PBS/Tween or the like from tank 1250, to be released into filter 1300. This is done prior to when the air sample enters first chamber 110 of each of the test units 100/200 of microfluidic cassette 1100. The eluent is preferably PBS/Tween (i.e. Phosphate Buffer Saline with detergent Tween), but the eluent can instead be BUF031A 10×ELISA wash buffer, PBST 10×, or a liquid containing Triton-X100 detergent or the like. The purpose of the eluent is to remove the analyte (i.e. the air sample containing the biological contaminant suspended in plume 7000) from the absorbent (i.e. filter 1300) and to move the elute containing the analyte into first chamber 110 via inlet 160 at proximal end 180 of each test unit 100/200 of microfluidic cassette 1100.

As illustrated in FIGS. 2A and 4, when the eluent containing the analyte air sample reaching the first chamber 110/210 of the test unit 100/200 of microfluidic cassette 1100, the eluent mixes with the lyophilized Arcis™ reagent 1 (lysis buffer) or the like, such that the Arcis™ reagent 1 lyses cells within the eluent. Specifically, the lysis reaction dissolves the cell membranes and opens the analyte cells to release the analyte DNA, thereby producing a lysate. This first Arcis™ reagent also chelates the DNA. After about one minute of processing time in first chamber 110, valve 120 opens and releases the lysate from first chamber 110 into second chamber 130/230, where the lysate is allowed to mix with a lyophilized Arcis™ reagent 2 (wash buffer) or the like to prepare the lysate for DNA amplification. The purpose of this second Arcis™ reagent (i.e. Arcis™ Reagent 2) is to remove the nucleic acid chelation, relax the DNA so that amplification target sites can be easily accessed, and remove anything that could inhibit the subsequent LAMP reaction. The second Arcis™ reagent may contain a proprietary buffer to eliminate any inhibitors that may have been carried over from the first chamber.

Valve 120/220 opens automatically due to the centrifugal force produced by AABAD 1000 while spinning and descending to the ground at a speed of at least about 1800 rpm, preferably of at least about 2000 rpm, and more preferably of at least about 2500 rpm. Valve chamber 120 may be in the form of an electromagnetic gate, or in the form of a metering trap 220 in the test unit 200 according to a second embodiment of the present invention as illustrated in FIG. 4.

After about at least 5 seconds of processing time within second chamber 130/230, a second valve 140, which is preferably a metering trap or the like, opens up to release the conditioned sample from the second chamber 130/230 to progress into LAMP reactor 150 wherein the conditioned sample mixes with a fluorescent dye and the DNA specific to at least one biological agent is amplified. LAMP reactor 150 includes a heater (not illustrated) to heat the LAMP reactor 150 and the conditioned sample therein to 65° C. for 12 minutes. The heater is located underneath LAMP reactor 150 while being connected to PCB 1400. A fluorescent dye is present in LAMP reactor 150 in either the form of a heat dissolving pill or dehydrated and attaches to the amplified target DNA upon the analyte reaching LAMP reactor 150, and thereafter the sample exits LAMP reactor 150 via outlet 170 and proceeds to a detection module 1420. While within detection module 1420, the amplified sample is irradiated with light from an LED 1430, and a detector within detection module 1420 detects whether the DNA for the specified biological target is present within the sample, by detecting for a presence of a fluorescence produced by the fluorescent dyes attached to the amplified target DNA reacting with the LED light.

Following the detection, microcontroller 1410 interprets the detection results, and communications the results of the tests to a remote location. This remote location may be an aircraft 6000 that releases the AABADs 1000, or a distant wireless receiver. Communications can be achieved by radio communications, or light-based Morse code such as a flashing visible or infrared LED. A transmitter may be located within supplemental PCB 1407 or electronic module 1200. Sample collection, preparation, analysis and reporting are all completely automated and occur within 15 minutes, of which the LAMP reaction takes approximately 12 minutes. AABAD 1000 is to remain airborne and spinning at a rapid rate of approximately at least 1800 rpm, preferably at least 2000 rpm and more preferably 2500 rpm throughout the collection phase and sample preparation phase which takes several minutes. The isothermal amplification in the LAMP reactor 150, detection, data interpretation and the wireless transmission of the results may occur after the AABAD's arrives on ground 4000.

Subsequent to the wireless transmission of the results to the aircraft 6000 or to some other location, the microcontroller 1410 can activate the kill switch (see FIG. 3) to destroy the AABAD 1000. This is to prevent other personnel from touching the used AABAD 1000 because the used AABAD may have been contaminated by the biohazards of plume 7000. The kill switch may be a heater or the like that destroys AABAD 1000 and any biological agents thereon.

The system 9000 according to the present invention of FIGS. 2A/2B to 5 allows for automatic collection of a sample and automatic cell lysis of the collected sample. In the present invention, the AABAD 1000 and system 9000 allow for automated collection and cell lysis to occur so that no human has to be placed in harms' way. Furthermore, these processes of sample collection and cell lysis are integrated with the other processes of lysate conditioning, LAMP amplification, detection and transmission of results. This provides a very rapid, safe and efficient means to determine whether or not a plume 7000 positioned near combat personnel 5000 on the ground 4000 poses a problem to said personnel and such a result can be safely, quickly and automatically achieved.

As a result, combat troops 5000 located near plume 7000 can be informed quickly as to whether plume 7000 presents any danger, allowing combat troops 5000 enough time to take evasive or protective measures before plume 7000 drifts towards combat troops 5000. Also, aircraft or UAV 6000 can be spared having to come into contact with plume 7000, allowing the aircraft or UAV to be reused. Furthermore, by dispersing a large number of AABADs 1000 in an atmosphere in a vicinity of plume 7000, there is a smaller risk of obtaining a false negative conclusion as the probability increases that at least one of the AABAD's will successfully be able to collect an air sample from within plume 7000, process the same and transmit correct results to a remote location.

Example

A testing of the *Yersinia pestis* LAMP assay using Arcis™-prepped samples was conducted. A BSL-2 *Yersinia pestis* pgm-strain (Harbin 35) was streaked onto a tryptic soy agar ("TSA") plate and incubated for 72 hours at 28° C. A single, isolated colony was used to inoculate 5 mL tryptic soy broth ("TSB"), and the culture (Yp) was then incubated at 28° C. with shaking for 23 hours. Next, aliquots containing 30 µL of Yp culture were mixed with 120 µL Arcis™ reagent 1 (lysis buffer). The culture was also plated using serial dilutions to determine colony forming units ("CFU")/mL. The culture/lysis buffer mixtures were incubated at room temperature for 1 minute. The culture/lysis buffer mixtures were then used to prepare triplicate samples of each of the following ratios to Arcis™ reagent 2 (wash buffer): 1:2, 1:3, and 1:4. The aim was to determine which ratio would be optimal for the LAMP assay. LAMP primers targeting the Yp specific 3a chromosomal sequence designed by Feng, et al. were utilized with LAMP method known in the art. Triplicate samples for each Arcis™ reagent 2 ratio were tested to determine the optimal ratio for sample preparation. A negative control (NTC) using water instead of Arcis™-prepped *Yersinia pestis* sample was used along with a positive control (PTC) containing purified Yp pgm-strain (Harbin 35) DNA at a concentration of 0.4 ng/µL per reaction. The LAMP assay was run on an ABI 7900 instrument for 60 minutes at a constant temperature of 65° C.

Figure 6:
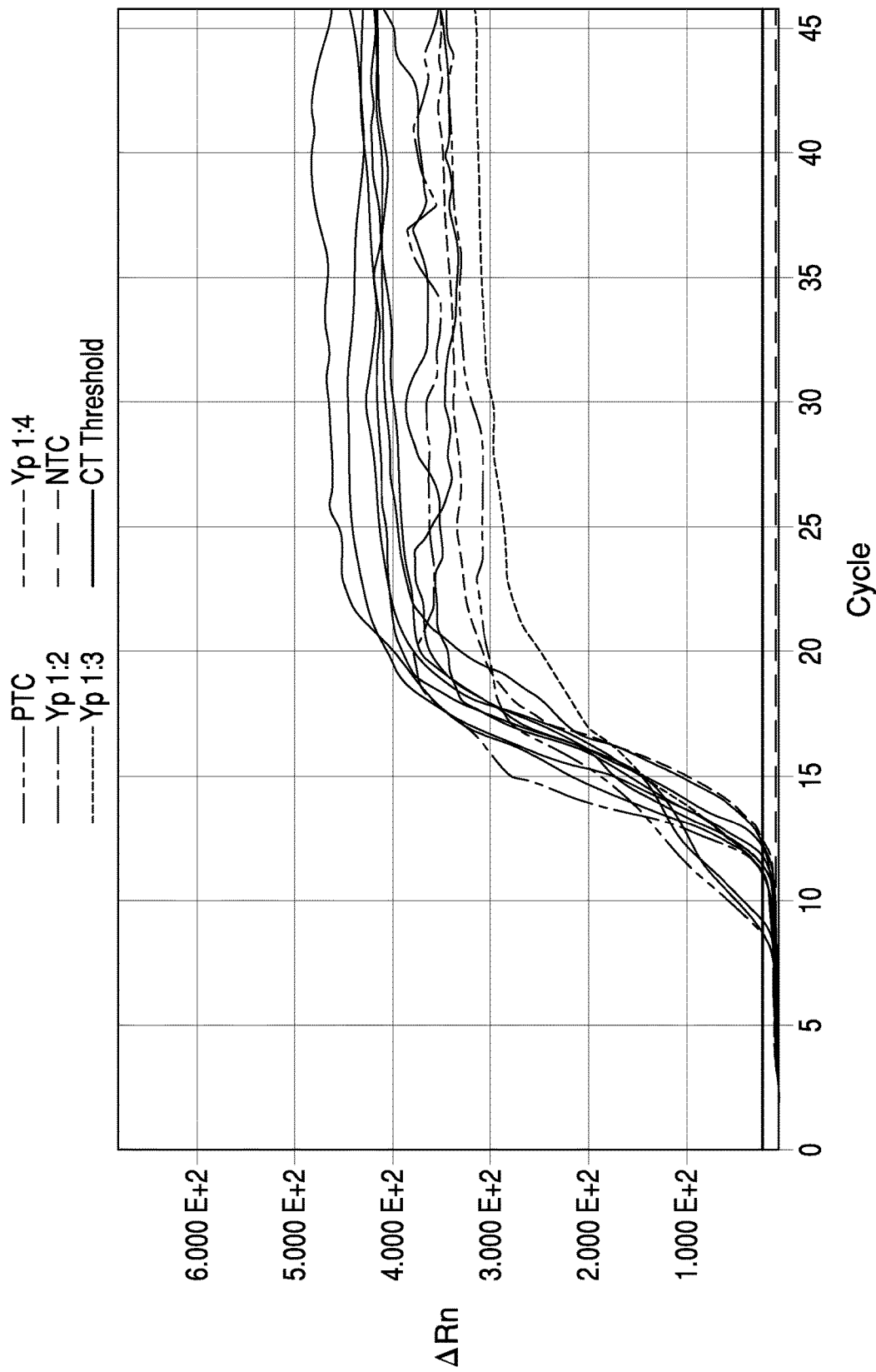
FIG. 6 illustrates a graph showing an amplification of *Yersinia pestis* in a LAMP assay according to various sample preparation ratios.

FIG. 6 is a graph of amplification curves showing results of various ratios of a culture (*Yersinia pestis* or Yp) lysis buffer mixtures to Arcis™ reagent 2 in an attempt to determine an optimal ratio for sample preparation for a LAMP reaction. As illustrated in FIG. 6, a wide range of ratios of lysate culture buffer mixture to Arcis™ reagent 2 resulted in DNA amplification in a LAMP reaction.

A test was subsequently conducted to measure an optimal rate of spinning (rpm) needed to move a testing sample through the microfluidic cassette of the present invention. It was observed that at a constant centrifugation speed of 1,000 rpm, the preloaded liquid in the lysis chamber remained in the chamber, while the liquid in the wash chamber moved. However, it was observed that at 2,500 rpm all preloaded liquids moved successfully through the cassette.

The invention claimed is:

1. An aerodynamic automated biological assay device ("AABAD"), comprising:
    a substrate having a top surface, a bottom surface, a first distal end, a second end opposing said first distal end; a center of mass located adjacent to said second opposing end, and a center of lift located near a geometric center of said substrate;
    an electronic module located on said top surface of said substrate adjacent to said second opposing end, said electronic module including a power source, and an electronics package; and
    a microfluidic cassette located on said top surface of said substrate between said second opposing end and said center of lift, wherein said microfluidic cassette performs an assay to analyze contents of an air sample collected from the earth's atmosphere, and wherein said assay is induced via a centrifugal force that is produced along a length of said microfluidic cassette without motor or active propulsion system, by said first distal end autorotating about said second opposing end due to airflow when said AABAD is descending through the atmosphere from an elevated height.

2. The AABAD of claim 1, wherein said AABAD further comprises:
    a collection filter located on said top surface of said substrate and adjacent to said microfluidic cassette, to collect said air sample;
    a buffer tank having a fluid to elute the collected air sample from said collection filter into said microfluidic cassette;
    a light source adjacent to said microfluidic cassette opposite said collection filter, to irradiate a processed air sample from said microfluidic cassette;
    a detection module having a light detector that detects the presence of at least one fluorescent dye attached to at least one biological agent in said assay; and,
    a transmitter that wirelessly transmits detected results from said light detector to a remote location.

3. The AABAD of claim 1, wherein said substrate has a shape in the form of a maple (acer) seed/fruit (samara), a bird wing, and airplane wing or an air foil, such that said substrate has a leading edge and a trailing edge opposing said leading edge, each of said leading edge and said trailing edge extend from said first distal end to said second opposing end.

4. The AABAD of claim 1, wherein said electronic module is heavier in weight than said substrate and said microfluidic cassette, and the center of mass is disposed near said electronic module.

5. The AABAD of claim 3, wherein a portion of said substrate near said leading edge has a greater mass than a portion of said trailing edge, wherein said first distal end of said substrate spins about said second opposing end in full 360 degrees in a direction such that said trailing edge trails said leading edge.

6. The AABAD of claim 1, wherein said substrate is comprised of a material selected from a group consisting of paper, Styrofoam, metal, plastic and mixtures thereof.

7. The AABAD of claim 1, wherein said substrate autorotates at a speed of at least 1800 rpm when dropped from an elevated height between 33,000 and 1,000 feet.

8. The AABAD of claim 1, wherein said substrate autorotates at a speed of at least 2500 rpm when dropped from an elevated height between 33,000 and 1,000 feet.

9. The AABAD of claim 1, wherein said microfluidic cassette comprises at least two test units arranged in parallel to one another and extending in a direction parallel to a line extending from said first distal end to said second opposing end of said substrate.

10. The AABAD of claim 9, wherein each of said test units comprises a plurality of chambers, wherein each of said chambers are spaced-apart by a valve, said valve is in the form of an electromagnetic gate and/or a metering trap.

11. The AABAD of claim 10, wherein said centrifugal force induces a first chamber of each said test unit, located near said first distal end of said substrate, to perform cell lysis of said air sample to produce a lysate, and induces a second chamber of each said test unit, connected to said first chamber via a valve, to amplify DNA from said lysate received from said first chamber.

12. The AABAD of claim 11, wherein said DNA is amplified by a loop-mediated isothermal nucleic acid amplification ("LAMP") technique.

13. The AABAD of claim 11, wherein said second chamber includes a dye so that fluorescence generated from said dye attached to at least one biological agent is used to detect said biological agent.

14. The AABAD of claim 13, wherein said assay and said detection occur within 15 minutes of receiving said air sample.

15. The AABAD of claim 1, wherein AABAD tests for at least one biological agent selected from a group consisting of *Yersinia pestis, Bacillus anthracis, Francisella tularensis, Clostridium botulinum, Listeria monocytogenes, Burkholderia mallei, Shigella dysenteriae, Corynebacterium diphtheriae, Vibrio cholerae, Brucella suis, Brucella melitensis, Brucella abortus*, and mixtures thereof.

16. The AABAD of claim 10, wherein said valve is a meter trap located between said chambers to control timing and fluidic volume.

17. A method for detecting the presence of at least one biological agent suspended in the earth's atmosphere, comprising:
    a) releasing one or more one aerodynamic automated biological assay devices (AABADs) into the earth's atmosphere from an elevated height, wherein said AABADs comprise:
        a substrate having a top surface, a bottom surface, a first distal end, a second end opposing said first distal end; a center of mass located adjacent to said second opposing end, and a center of lift located near a geometric center of said substrate;
        an electronic module located on said top surface of said substrate adjacent to said second opposing end, said electronic module including a power source, and
        a microfluidic cassette located on said top surface of said substrate between said second opposing end and said center of lift, wherein said microfluidic cassette performs an assay to analyze contents of an air sample collected from the earth's atmosphere, b) collecting at least one air sample from the earth's atmosphere as the one or more AABADs rotate during their descent to the ground due to airflow and aerodynamic forces and without a motor or other power source to cause rotation, c) analyzing said collected air sample by passing the sample through said microfluidic cassette while said AABADs are airborne and rotating; and d) communicating wirelessly from said one or more AABADs to a remote site results of the analysis of said air samples, wherein said collection and said analysis are induced via a centrifugal force that is produced along a length of said microfluidic cassette by said first distal end autorotating about said second opposing end due to aerodynamic forces when said AABADs are descending through the atmosphere from an elevated height.

18. The AABAD of claim 17, wherein said microfluidic cassette comprises at least two test units arranged in parallel to one another and extending in a direction parallel to a line extending from said first distal end to said second opposing end of said substrate.

19. The AABAD of claim 18, wherein each of said test units comprises a plurality of chambers, wherein each of said chambers are spaced-apart by a valve, said valve is in the form of an electromagnetic gate and/or a metering trap.

20. The method of claim 17, wherein said analysis comprises:

a) mixing said collected air sample with an eluent to produce an eluate that progresses into a first chamber of said microfluidic cassette;

b) lysing said eluate to produce a lysate from said eluate in said first chamber;

c) amplifying said lysate in a second chamber of said microfluidic cassette according to a loop-mediated isothermal nucleic acid amplification ("LAMP") technique;

d) mixing a dye with said amplified lysate; and e) detecting fluorescence from said amplified sample to detect the presence of DNA corresponding at least one biological agent.

21. The method of claim 17, wherein said detection occurs within 15 minutes of said collection of said air sample.

22. The method of claim 17, wherein said at least one AABAD was dropped into the earth's atmosphere from an elevated height by a manned or an unmanned aerial vehicle (UAV).

* * * * *